United States Patent [19]
Prashad et al.

[11] Patent Number: 5,606,053
[45] Date of Patent: Feb. 25, 1997

[54] PROCESS FOR PREPARING 1,1'-[1,4-PHENYLENEBIS-(METHYLENE)]-BIS-1,4,8,11-TETRAAZACYCLOTETRADECANE

[75] Inventors: Mahavir Prashad, Hopatcong; Prasad Kapa, Parsippany, both of N.J.

[73] Assignee: Johnson Matthey PLC, London, England

[21] Appl. No.: 434,142

[22] Filed: May 2, 1995

[51] Int. Cl.$^6$ .................. C07D 255/00; C07D 255/02
[52] U.S. Cl. ............................ 540/474; 540/470
[58] Field of Search ...................... 540/470, 474

[56] References Cited

U.S. PATENT DOCUMENTS

| | | | |
|---|---|---|---|
| 5,021,409 | 6/1991 | Murrer et al. | 514/183 |
| 5,047,527 | 9/1991 | Handel et al. | 540/474 |
| 5,326,861 | 7/1994 | Madison et al. | 540/474 |

FOREIGN PATENT DOCUMENTS

| | | |
|---|---|---|
| 374929 | 6/1990 | European Pat. Off. . |
| 9312096 | 6/1993 | WIPO . |

OTHER PUBLICATIONS

J. Med. Chem., vol. 38, No. 2, pp. 366–378 (1995).

*Primary Examiner*—Mukund J. Shah
*Assistant Examiner*—Pavanaram K. Sripada
*Attorney, Agent, or Firm*—Cushman Darby & Cushman IP Group Pillsbury Madison & Sutro LLP

[57] ABSTRACT

An improved process for preparing 1,1'-[1,4-phenylenebis-(methylene)]-bis-1,4,8,11-tetraazacyclotetradecane comprising the selective functionalization of an acyclic tetraamine to obtain an acyclic ditosyl intermediate and an acyclic tritosyl intermediate in a first step, the independent dimerization/tosylation of the ditosyl intermediate and dimerization of the tritosyl intermediate to obtain a 1,4-phenylenebis-methylene bridged hexatosyl acyclic precursor in a second step, the cyclization of said precursor to obtain a hexatosyl cyclam dimer in a third step, and the detosylation of said cyclam dimer in a fourth step followed by basification to obtain the desired 1,1'-[1,4-phenylenebis-(methylene)]-bis-1,4,8,11-tetraazacyclotetradecane.

19 Claims, No Drawings

PROCESS FOR PREPARING 1,1'-[1,4-PHENYLENEBIS-(METHYLENE)]-BIS-1,4,8,11-TETRAAZACYCLOTETRADECANE

BACKGROUND OF THE INVENTION

1. Field of the Invention

The present invention relates to the area of cyclam dimers and, more particularly, relates to an improved process for preparing a specific pharmaceutically active 1,4-phenylene-bis-(methylene)-linked cyclam dimer.

2. Description of the Prior Art

U.S. Pat. No. 5,021,409 is directed to a method of treating retroviral infections comprising administering to a mammal in need of such treatment a therapeutically effective amount of a bicyclic macrocyclic polyamine compound. Although the usefulness of certain alkylene and arylene bridged cyclam dimers is generically embraced by the teachings of the reference, no arylene bridged cyclam dimers are specifically disclosed.

WO 93/12096 discloses the usefulness of certain linked cyclic polyamines in combating HIV and pharmaceutical compositions useful therefor. Among the specifically disclosed compounds is 1,1'-[1,4-phenylenebis-(methylene)]-bis-1,4,8,11 tetraazacyclotetradecane (and its acid addition salts), which compound is a highly potent inhibitor of several strains of human immune deficiency virus type 1 (HIV-1) and type 2 (HIV-2).

European Patent Appln. 374,929 discloses a process for preparing mono-N-alkylated polyazamacrocycles comprising reacting the unprotected macrocycle with an electrophile in a non-polar, relatively aprotic solvent in the absence of base. Although it is indicated that the monosubstituted macrocycle is formed preferentially, there is no specific disclosure which indicates that linked bicyclams can be synthesized by this process.

U.S. Pat. No. 5,047,527 is directed to a process for preparing a monofunctionalized (e.g., monoalkylated)cyclic tetramine comprising: 1) reacting the unprotected macrocycle with chromium hexacarbonyl to obtain a triprotected tetraazacycloalkane compound; 2) reacting the free amine group of the triprotected compound prepared in 1) with an organic (e.g., alkyl) halide to obtain a triprotected monofunctionalized (e.g., monoalkylated) tetraazacycloalkane compound; and 3) de-protecting the compound prepared in 2) by simple air oxidation at acid pH to obtain the desired compound. In addition, the reference discloses alternative methods of triprotection employing boron and phosphorous derivatives and the preparation of linked compounds, including the cyclam dimer 1,1'-[1,4-phenylenebis-(methylene)]-bis-1,4,8,11-tetraazacyclotetradecane, by reacting triprotected cyclam prepared as set forth in 1) above with an organic dihalide in a molar ratio of 2:1, and deprotecting the resultant compound to obtain the desired cyclam dimer.

J. Med. Chem., Vol. 38, No. 2, pgs. 366–378 (1995) is directed to the synthesis and anti-HIV activity of a series of novel phenylenebis(methylene)-linked bis-tetraazamacrocyclic analogs, including the known cyclam dimer 1,1'-[1,4-phenylenebis(methylene)]-bis-1,4,8,11-tetraazacyclotetradecane. The cyclam dimers disclosed in this reference, including the afore-mentioned cyclam dimer, are prepared by: 1) forming the tritosylate of the tetraazamacrocycle; 2) reacting the protected tetraazamacrocycle with an organic dihalide, e.g., dibromo-p-xylene, in acetonitrile in the presence of a base such as potassium carbonate; and 3) deprotecting the bis-tetraazamacrocycle prepared in 2) employing freshly prepared sodium amalgam, concentrated sulfuric acid or an acetic acid/hydrobromic acid mixture to obtain the desired cyclam dimer, or an acid addition salt thereof.

Although the processes disclosed in U.S. Pat. No. 5,047,527 and the J. Med. Chem. reference are suitable to prepare the cyclam dimer 1,1'-[1,4-phenylenebis-(methylene)]-bis-1,4,8,11-tetraazacyclotetradecane, they involve the use of cyclam as a starting material, a compound which is expensive and not readily available. Accordingly, in view of its potent anti-HIV activity, a number of research endeavors have been undertaken in an attempt to develop a more practical process for preparing 1,1'-[1,4-phenylenebis-(methylene)]-bis-1,4,8,11-tetraazacyclotetradecane.

SUMMARY OF THE INVENTION

The present invention relates to a more efficient and economic process for preparing 1,1'-[1,4-phenylenebis-(methylene)]-bis-1,4,8,11-tetraazacyclotetradecane employing an inexpensive and readily available acyclic tetraamine compound as the starting material. More particularly, the present invention involves the selective functionalization of an acyclic tetraamine to obtain an acyclic ditosyl intermediate and an acyclic tritosyl intermediate in a first step, the independent dimerization/tosylation of the ditosyl intermediate and dimerization of the tritosyl intermediate to obtain a 1,4-phenylenebis-methylene bridged hexatosyl acyclic precursor in a second step, the cyclization of said precursor to obtain a hexatosyl cyclam dimer in a third step, and the detosylation of said cyclam dimer in a fourth step followed by basification to obtain the desired 1,1'-[1,4-phenylenebis-(methylene)]-bis-1,4,8,11 -tetraazacyclotetradecane.

DETAILED DESCRIPTION OF THE INVENTION

The present invention relates to an improved process for preparing 1,1'-[1,4-phenylenebis-(methylene)]-bis-1,4,8,11-tetraazacyclotetradecane by a three-step process as depicted below:

Step 1
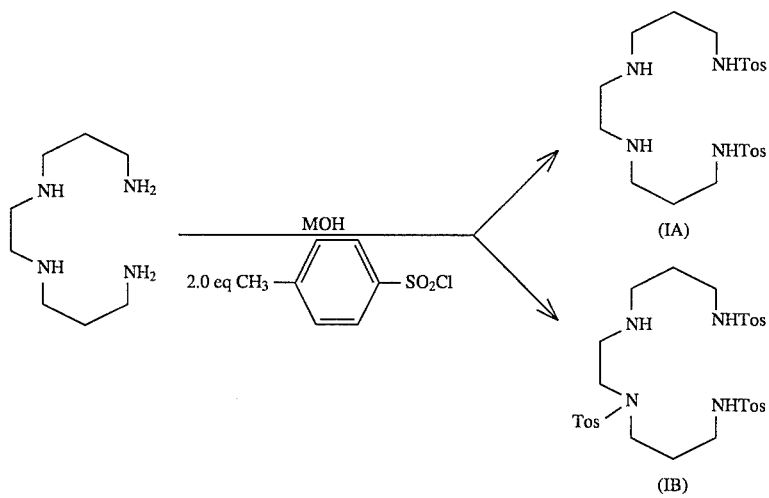
where M is an alkali metal.
Step 2A
Part 1
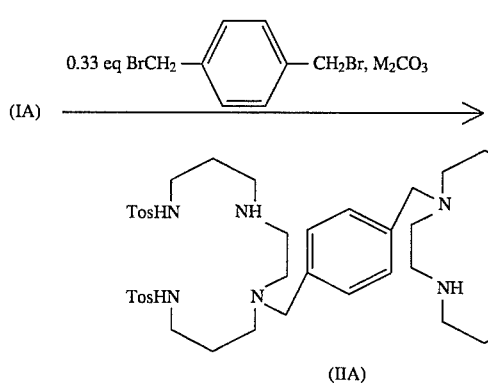
Part 2
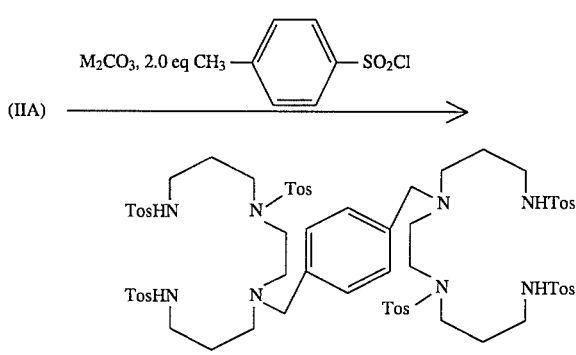
where M is as defined above.
Step 2B
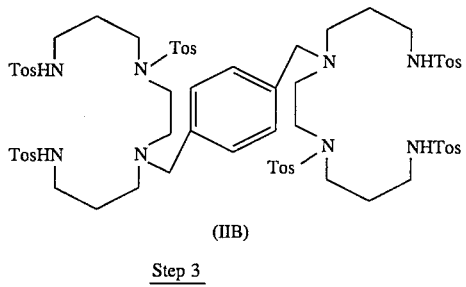
Step 3
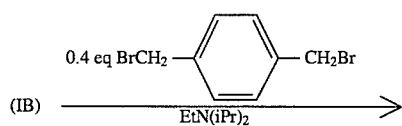
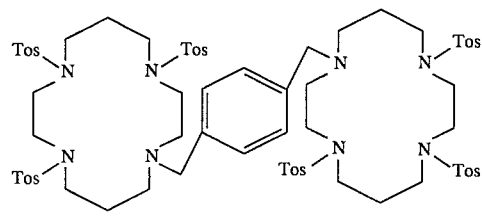
where M is as defined above.
Step 4

Step 4

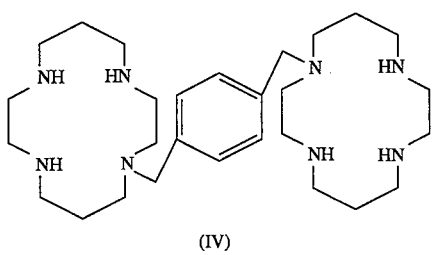

where M is as defined above.

With respect to the individual steps, Step 1 concerns the reaction of N,N'-bis(3-aminopropyl)ethylenediamine with 2 equivalents of p-toluenesulfonylchloride in the presence of an alkali metal hydroxide such as sodium hydroxide to yield the acyclic ditosylate compound of formula IA and the acyclic tritosylate compound of formula IB. The tosylation is carried out in the presence of an aromatic hydrocarbon such as toluene at a temperature of from 5° C. to 40° C. for a period of between 2 and 5 hours.

Step 2A, in a first part, involves subjecting the ditosylate compound prepared in Step 1, i.e., the compound of formula IA, to dimerization by reacting it with 0.33 equivalents of α,α'-dibromo-p-xylene in the presence of an alkali metal carbonate such as potassium carbonate to obtain the 1,4-phenylenebis-methylene bridged tetratosyl acyclic dimer of formula IIA. The dimerization is carried out in a mixture of a cyclic ether such as tetrahydrofuran and a lower alkanol such as methanol at a temperature of from 0° C. to 45° C. for a period of between 2 and 6 hours.

The second part of Step 2A concerns the tosylation of the compound prepared in the first part, i.e., the tetratosyl acyclic dimer of formula IIA, by reacting it with 2 equivalents of p-toluenesulfonylchloride in the presence of an alkali metal carbonate such as potassium carbonate to obtain the 1,4-phenylenebis-methylene bridged hexatosyl acyclic dimer of formula IIB. The tosylation is carried out in the presence of a cyclic ether such as tetrahydrofuran at a temperature of from 15° C. to 35° C. for a period of between 1 and 4 hours.

Step 2B involves subjecting the tritosylate compound prepared in Step 1, i.e., the compound of formula IB, to dimerization by reacting it with 0.4 equivalents of α,α'-dibromo-p-xylene in the presence of diisopropylethylamine to obtain the 1,4-phenylenebis-methylene bridged hexatosyl acyclic dimer of formula II. The dimerization is carried out in the presence of a cyclic ether such as tetrahydrofuran at a temperature of from 10° C. to 45° C. for a period of between 6 and 20 hours.

Step 3 concerns the cyclization of the compound prepared in the second part of Step 2A and in Step 2B, i.e., the bridged hexatosyl acyclic dimer of formula IIB, by reacting it with 3 equivalents of ethyleneglycol ditosylate in the presence of a mixture of an alkali metal hydroxide such as sodium hydroxide (in bead form) and an alkali metal carbonate such as potassium carbonate (in anhydrous form) and a catalytic amount of t-butylammonium sulfate to obtain the hexatosyl cyclam dimer of formula III. The cyclization is carried out in the presence of dimethylformamide at a temperature of from 75° C. to 125° C. for a period of between 4 and 7 hours.

Alternatively, the bridged hexatosyl acyclic dimer of formula IIB can be reacted with 3 equivalents of ethyleneglycol ditosylate in the presence of cesium carbonate in dimethylformamide at a temperature of from 75° C. to 125° C. for a period of between 4 and 7 hours to obtain the hexatosyl cyclam dimer of formula III.

Step 4 concerns the detosylation of the compound prepared in Step 3, i.e., the hexatosyl cylam dimer of formula III, by reacting it with a mixture of hydrobromic acid (48% solution) and glacial acetic acid. The product is then basified with an alkali metal hydroxide solution (e.g., a 3N sodium hydroxide solution) to obtain the desired compound of formula IV. The detosylation is carried out at reflux temperature for a period of between 30 hours and 3 days. Alternatively, the detosylation may be carried out by reacting the compound prepared in Step 3 with concentrated sulfuric acid or with a mixture of sodium phosphate and freshly prepared sodium amalgam in an argon atmosphere. The detosylation with concentrated sulfuric acid may be carried out at a temperature of from 80° C. to 120° C. for a period of between 2 and 5 hours, whereas the detosylation with a mixture of sodium phosphate and sodium amalgam may be carried out at a temperature of from 80° C. to 120° C. for a period of between 1 and 4 days.

As alluded to above, the acyclic tetraamine compound employed as the starting material in Step 1 is known and commercially available:

Although the product of each reaction described above in Step 1, the two parts of Step 2A, Step 2B and Step 3 may, if desired, be purified by conventional techniques such as recrystallization (if a solid), the crude product of one reaction is advantageously employed in the following reaction without purification.

It should be understood that although the instant process is directed to the preparation of the highly potent anti-HIV cyclam dimer 1,1'-[1,4-phenylenebis-(methylene)]-bis-1,4, 8,11-tetraazacyclotetradecane in free base form, said compound can be readily converted to pharmaceutically acceptable acid addition salt forms, if desired, in conventional manner. For example, the free base can be reacted with hydrobromic acid to obtain the cyclam dimer in octahydrobromide dihydrate form. Similarly, the addition of saturated hydrochloric acid to the free base yields the cyclam dimer in octahydrochloride dihydrate form.

The bridged tetratosyl acyclic precursor of formula IIA is a novel compound and, as such, also forms a part of this invention.

The following examples are for purposes of illustration only and are not intended to limit in any way the scope of the instant invention.

EXAMPLE 1 a) Preparation of the acyclic ditosylate compound of formula IA.

In a 4-necked, round-bottomed flask, equipped with a mechanical stirrer, cooling bath, internal thermometer and addition funnel, a suspension of 69.7 g. (0.4 mol) of N,N'-bis-(3-aminopropyl)ethylenediamine, 400 ml. of toluene and 640 ml. (8.0 mol) of a 50% sodium hydroxide solution is cooled to 13° C. To the cooled suspension is then added, over a period of 45 minutes while the temperature is maintained at between 13° C. and 15° C., a solution of 152.52 g. (0.8 mol) of p-toluenesulfonylchloride in 250 ml. of toluene. The reaction mixture is then warmed to 22° C. over a period of 90 minutes, after which time 1 liter of water is added while the temperature is maintained at between 22° C. and 24° C. To the resultant mixture is added 1.5 liters of n-butanol and the pH is adjusted to 8 from 12 with concentrated hydrochloric acid, while the temperature is maintained at between 22° C. and 24° C. The organic layer is then separated and the aqueous layer is extracted with 250 ml. of n-butanol. The combined organic layer is washed with 500 ml. of water, dried over anhydrous magnesium sulfate and concentrated in vacuo. The resultant thick paste is then triturated with 650 ml. of acetonitrile and the solid is collected by filtration. The solid is then washed with two 50 ml. portions of acetonitrile and dried at 70° C. under vacuum (20–25 mmHg) to yield the desired ditosylate compound.

b) Preparation of the acyclic tritosylate compound of formula IB.

The filtrate from a) above is concentrated to yield a syrup in crude form. The crude syrup is then chromatographed on silica gel employing a mixture of dichloromethane and methanol (in a ratio of 95:5) as the eluant. The fractions containing the tritosylate are combined and concentrated in vacuo to yield the desired tritosylate compound as a syrup.

c) Preparation of the 1,4-phenylenebis-methylene bridged tetratosyl acyclic dimer of formula IIA.

In a 4-necked, round-bottom flask, equipped with a magnetic stirrer, cooling bath, internal thermometer and addition funnel, 1.8 g. (3.73 mmol) of the ditosylate compound prepared in a) above is dissolved in 20 ml. of tetrahydrofuran and 10 ml. of methanol by slight heating. The solution is then cooled in an ice bath and to the cooled solution is added 0.69 g. (5.0 mmol) of potassium carbonate and 0.33 g. (1.25 mmol) of α,α'-dibromo-p-xylene. The reaction mixture is then warmed to room temperature and, with stirring, maintained at room temperature for 3½ hours. The solvents are evaporated to yield the desired compound as a crude residue.

d) Preparation of the 1,4-phenylenebis-methylene bridged hexatosyl acyclic dimer of formula IIB.

The crude residue obtained in c) above is treated with 25 ml. of tetrahydrofuran, after which time 1.03 g. (7.47 mmol) of potassium carbonate and 1.424 g. (7.47 mmol) of p-toluenesulfonylchloride is added. The resultant mixture is then stirred at room temperature for 2 hours and then concentrated in vacuo. The crude residue is then treated with 50 ml. of water and extracted with 70 ml. of ethyl acetate. The organic layer is then dried over anhydrous magnesium sulfate and concentrated in vacuo. The resultant residue is then purified by silica gel chromatography employing a mixture of hexane and ethyl acetate (in a ratio range of 50:50 to 30:70) as the first eluant and then pure ethyl acetate as the second eluant. The combined fractions are then concentrated in vacuo to yield the desired compound.

EXAMPLE 2

Preparation of the 1,4-phenylenebis-methylene bridged hexatosyl acyclic dimer of formula IIB employing the tritosylate compound of formula IB.

A solution of 3.18 g. (5.0 mmol) of the compound prepared in Example 1b) above and 0.78 g. (6.0 mmol) of N,N-diisopropylethylamine in 20 ml. of tetrahydrofuran is cooled in an ice bath and to the cooled solution is added 0.594 g. (2.25 mmol) of α,α'-dibromo-p-xylene. The resultant mixture is warmed to room temperature and maintained at this temperature for 15 hours. The reaction mixture is then concentrated in vacuo and the crude residue is treated with 100 ml. of ethyl acetate. The resultant solution is then washed successively with 60 ml. of water, 60 ml. of 1N hydrochloric acid and 60 ml. of water. The organic layer is then dried over anhydrous magnesium sulfate and concentrated in vacuo. The crude residue is then purified by silica gel chromatography employing a mixture of hexane and ethyl acetate (in a ratio range of 50:50 to 30:70) as the eluant. The combined fractions are then concentrated in vacuo to yield the desired compound.

EXAMPLE 3 a) Preparation of the hexatosyl cyclam dimer of formula III.

To a 4-necked, round-bottom flask, equipped with a magnetic stirrer, heating bath, internal thermometer and addition funnel, is added 1.98 g. (0.00144 mol) of the compound prepared in Example 1d) and Example 2 above and 50 ml. of dimethylformamide. After the system is degassed, 0.40 g. (0.010 mol) of NaOH beads, 0.47 g. (0.0034 mol) of anhydrous potassium carbonate and 0.09 g. (0.00027 mol) of t-butylammonium sulfate are added to the solution, and the resultant mixture is heated to 100° C. and maintained at this temperature for 2.5 hours. A solution of 0.19 g. (0.0051 mol) of ethyleneglycol ditosylate in 25 ml. of dimethylformamide is then added, over a period of 2 hours, while the temperature is maintained at 100° C. After cooling the reaction mixture to room temperature, it is poured into 75 ml. of water with stirring. The suspension is then filtered and the filter cake is washed with 25 ml. of water. The filter cake is then thoroughly mixed with 25 ml. of water and 50 ml. of ethyl acetate. The solvent is then removed from the ethyl acetate solution and the residue is re-dissolved in 15 ml. of warm acetonitrile. The precipitate that forms on standing is collected by filtration and then dried to yield the desired compound as a white solid.

b) Preparation of 1,1'-[1,4-phenylenebis-(methylene)]-bis, 1,4,8,11-tetraazacyclotetradecane.

In a 4-necked, round-bottom flask, equipped with a magnetic stirrer, heating bath, internal thermometer and addition funnel, is added 0.46 g. (0.00034 mol) of the compound prepared in a) above, 10 ml. of 48% hydrobromic acid and 25 ml. of glacial acetate acid. The resultant mixture is then heated to reflux and maintained at reflux temperature, with stirring, for 42 hours. The reaction mixture is then cooled to between 22° C. and 23° C. over a period of 4 hours, after which time it is stirred for an additional 12 hours. The solids are then collected using suction filtration and added to 15 ml. of deionized water. The resultant solution is then stirred for 25 to 30 minutes at a temperature between 22° C. and 23° C. and filtered using suction filtration. After washing the filter pad with a small amount of deionized water, the solution is cooled to between 10° C. and 15° C. 4.3 g. of a 50% aqueous solution of sodium hydroxide is then added, over a period of 30 minutes, while the temperature is maintained at between 5° C. and 15° C. The resultant suspension is stirred for 10 to 15 minutes, while the temperature is maintained at between 10° C. and 15° C. The suspension is then warmed to between 22° C. and 23° C. and to the warmed suspension is added 35 ml. of dichloromethane. The mixture is then stirred for 30 minutes, the layers are separated and the organic layer is slurried with 2 g. of sodium sulfate for 1 hour. The solution is then filtered using suction filtration, and the filtrate is concentrated under reduced pressure (40°–45° C. bath temperature, 70–75 mm Hg) until approximately 30 ml. of solvent is collected. To the slurry is then added 30 ml. of acetone, and the filtrate is concentrated under reduced pressure (40°–45° C. bath temperature, 70–75 mm Hg) until approximately 30 ml. of solvent is collected. The slurry is then cooled to between 22° C. and 23° C. and the solids are collected using suction filtration. The solids are then washed with three 2 ml. portions of acetone and dried in a vacuum oven to obtain the desired compound as a white solid.

What is claimed is:

1. A process for preparing 1,1'-[1,4-phenylenebis-(methylene)]-bis-1,4,8,11-tetraazacyclotetradecane comprising the steps of:
   1) selectively functionalizing an acyclic tetramine in a first step;
   2) independently dimerizing/tosylating the ditosyl intermediate prepared in the first step and dimerizing the tritosyl intermediate prepared in the first step;
   3) cyclizing the bridged hexatosyl acyclic precursor prepared in the second step; and
   4) detosylating the hexatosyl cyclam dimer prepared in the third step and basifying to obtain the 1,1'-[1,4-phenylenebis-(methylene)]-bis-1,4,8,11-tetraazacyclotetradecane.

2. A process according to claim 1 comprising the steps of:
   1) reacting N,N'-bis(3-aminopropyl)ethylene diamine with 2 equivalents of p-toluenesulfonylchloride to obtain the acyclic ditosylate compound of formula IA and the acyclic tritosylate compound of formula IB

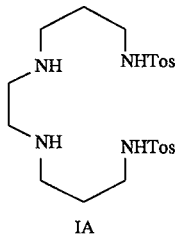 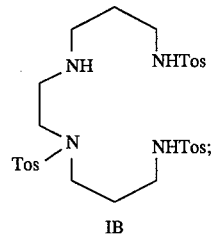

IA      IB 2a) in a first part a), dimerizing the ditosylate compound prepared in the first step by reacting it with 0.33 equivalents of α,α'-dibromo-p-xylene to obtain the 1,4-phenylenebis-methylene bridged tetratosyl acyclic dimer of formula IIA

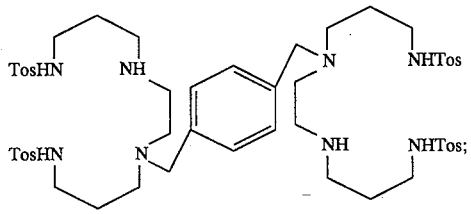

and in a second part b), tosylating the bridged tetratosyl acyclic dimer prepared in part a) by reacting it with 2 equivalents of p-toluenesulfonylchloride to obtain the 1,4-phenylene-bis-methylene bridged hexatosyl acyclic dimer of formula IIB

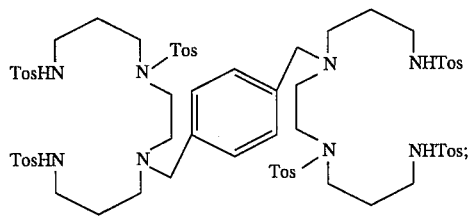

2b) dimerizing the tritosylate compound prepared in the first step by reacting it with 0.4 equivalents of α,α'-dibromo-p-xylene to obtain the hexatosyl acyclic dimer of formula IIB above;

3) cyclizing the bridged hexatosyl acyclic dimer prepared in the second part of Step 2a) and in Step 2b) by reacting it with 3 equivalents of ethyleneglycol ditosylate to obtain the hexatosyl cyclam dimer of formula III

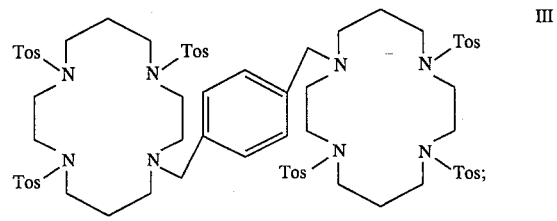

and 4) detosylating the hexatosyl cyclam dimer prepared in the third step and basifying the reaction mixture to obtain 1,1'-[1,4-phenylenebis-(methylene)]-bis-1,4,8,11-tetraazacyclotetradecane of formula IV

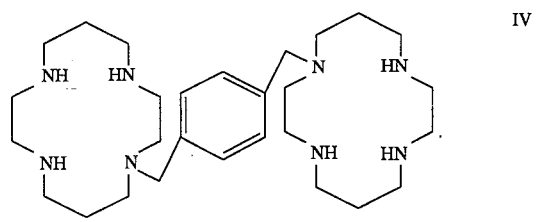

3. A process according to claim 2 wherein the first step is carried out in the presence of an alkali metal hydroxide and an aromatic hydrocarbon at a temperature of from 5° C. to 40° C. for a period of between 2 and 5 hours.

4. A process according to claim 2 wherein the first part of Step 2a) is carried out in the presence of an alkali metal carbonate at a temperature of from 0° C. to 45° C. for a period of between 2 and 6 hours.

5. A process according to claim 4 wherein the first part of Step 2a) is additionally carried out in the presence of a mixture of a cyclic ether and a lower alkanol.

6. A process according to claim 2 wherein the second part of Step 2a) is carried out in the presence of an alkali metal carbonate and a cyclic ether at a temperature of from 15° C. to 35° C. for a period of between 1 and 4 hours.

7. A process according to claim 2 wherein Step 2b) is carried out in the presence of diisopropylethylamine and a cyclic ether at a temperature of from 10° C. to 45° C. for a period of between 6 and 20 hours.

8. A process according to claim 2 wherein the cyclization reaction of the third step is carried out in the presence of a mixture of an alkali metal hydroxide and an alkali metal carbonate and a catalytic amount of t-butylammonium sulfate.

9. A process according to claim 8 wherein the cyclization reaction is carried out in the presence of dimethylformamide at a temperature of from 75° C. to 125° C. for a period of between 4 and 7 hours.

10. A process according to claim 2 wherein the cyclization reaction of the third step is carried out in the presence of cesium carbonate.

11. A process according to claim 10 wherein the cyclization reaction is carried out in the presence of dimethylformamide at a temperature of from 75° C. to 125° C. for a period of between 4 and 7 hours.

12. A process according to claim 2 wherein the detosylation reaction of the fourth step is carried out with a mixture of hydrobromic acid and glacial acetic acid.

13. A process according to claim 12 wherein the detosylation reaction is carried out at reflux temperature for a period of between 30 hours and 3 days.

14. A process according to claim 2 wherein the basification in the fourth step is carried out with an alkali metal hydroxide.

15. A process for preparing 1,1'-[1,4-phenylenebis-(methylene)]-bis-1,4,8,11-tetraazacyclotetradecane comprising the steps of:

1) reacting N,N'-bis(3-aminopropyl)ethylene diamine with 2 equivalents of p-toluenesulfonylchloride in the presence of an alkali metal hydroxide and an aromatic hydrocarbon at a temperature of from 5° C. to 40° C. for a period of between 2 and 5 hours to obtain the acyclic ditosylate compound of formula IA and the acyclic tritosylate compound of formula IB

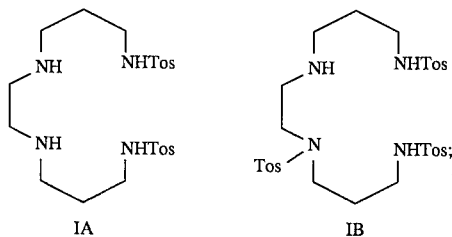

2a) in a first part a), dimerizing the ditosylate compound prepared in the first step by reacting it with 0.33 equivalents of α,α'-dibromo-p-xylene in the presence of an alkali metal carbonate and a mixture of a cyclic ether and a lower alkanol at a temperature of from 0° C. to 45° C. for a period of between 2 and 6 hours to obtain the 1,4-phenylenebis-methylene bridged tetratosyl acyclic dimer of formula IIA

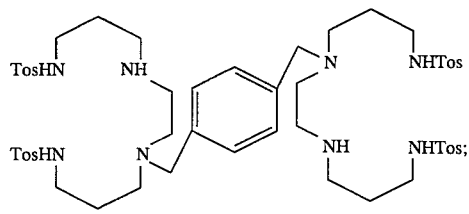

and in a second part b), tosylating the bridged tetratosyl acyclic dimer prepared in part a) by reacting it with 2 equivalents of p-toluenesulfonylchloride in the presence of an alkali metal carbonate and a cyclic ether at a temperature of from 15° C. to 35° C. for a period of between 1 and 4 hours to obtain the 1,4-phenylenebis-methylene bridged hexatosyl acyclic dimer of formula IIB

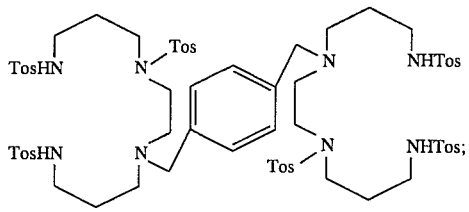

2b) dimerizing the tritosylate compound prepared in the first step by reacting it with 0.4 equivalents of a α,α-dibromo-p-xylene in the presence of diisopropylethylamine and a cyclic ether at a temperature of from 10° C. to 45° C. for a period of between 6 and 20 hours to obtain the hexatosyl acyclic dimer of formula IIB above;

3) cyclizing the bridged hexatosyl acyclic dimer prepared in the second part of Step 2a) and in Step 2b) by reacting it with 3 equivalents of ethyleneglycol ditosylate in the presence of a mixture of an alkali metal hydoxide and an alkali metal carbonate, a catalytic amount of t-butylammonium sulfate, and dimethylformamide at a temperature of from 75° C. to 125° C. for a period of between 4 and 7 hours to obtain the hexatosyl cyclam dimer of formula III

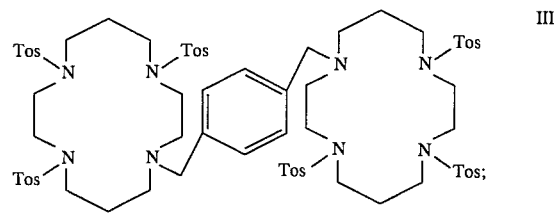

and 4) detosylating the hexatosyl cyclam dimer prepared in the third step by reacting it with a mixture of hydrobromic acid and glacial acetic acid at reflux temperature for a period of between 30 hours and 3 days, and then basifying the reaction mixture with an alkali metal hydroxide to obtain 1,1'-[1,4-phenylenebis-(methylene)]-bis-1,4,8,11-tetraazacyclotetradecane of formula IV

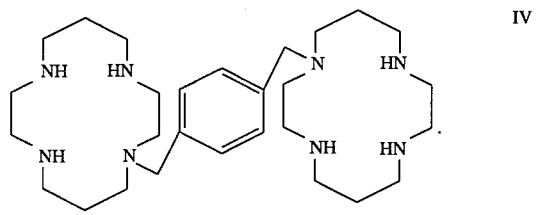

16. A process according to claim 2 wherein the detosylation reaction of the fourth step is carried out with concentrated sulfuric acid.

17. A process according to claim 16 wherein the detosylation reaction is carried out at a temperature of from 80° C. to 120° C. for a period of between 2 and 5 hours.

18. A process according to claim 2 wherein the detosylation reaction of the fourth step is carried out with a mixture of sodium phosphate and freshly prepared sodium amalgam in an argon atmosphere.

19. A process according to claim 18 wherein the detosylation reaction is carried out at a temperature of from 80° C. to 120° C. for a period of between 1 and 4 days.

* * * * *